(12) United States Patent
Chiu

(10) Patent No.: US 6,535,649 B1
(45) Date of Patent: Mar. 18, 2003

(54) DYNAMIC CALIBRATION METHOD

(75) Inventor: Chui-Kuei Chiu, Heng-Shan Hsiang (TW)

(73) Assignee: UMAX Data Systems Inc., Hsinchu (TW)

( * ) Notice: Subject to any disclaimer, the term of this patent is extended or adjusted under 35 U.S.C. 154(b) by 0 days.

(21) Appl. No.: 09/309,550

(22) Filed: May 11, 1999

(51) Int. Cl.$^7$ ................................................. G06K 9/40
(52) U.S. Cl. ...................... 382/274; 382/254; 358/406; 358/504
(58) Field of Search ................................. 358/406, 461, 358/463, 504; 382/254, 270, 271, 274, 272

(56) References Cited

U.S. PATENT DOCUMENTS 5,798,847 A * 8/1998 Aerts .......................... 358/461
6,198,845 B1 * 3/2001 Tse et al. ..................... 382/274

* cited by examiner

*Primary Examiner*—Thomas D. Lee
(74) *Attorney, Agent, or Firm*—Bacon & Thomas

(57) ABSTRACT

A method for dynamic calibration uses multi-sampling point distribution to analyze different distributions, then dynamically decides the total number of points counted and the best calculating method for the final calibration in order to get the most stable, accurate, and best calibrating result with different scanners and situation. Method of calculation include direct averaging, weighed average, multi-fixed-range averaging, and standard deviation range averaging.

15 Claims, 6 Drawing Sheets

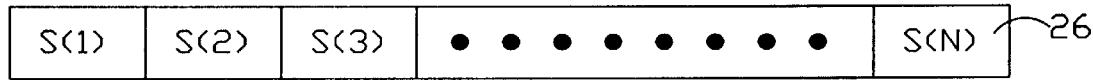
FIG.2(Prior Art)
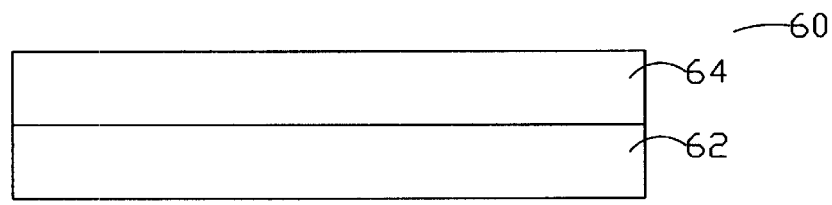
FIG.3(Prior Art)
| T(1,1) | T(1,2) | T(1,3) | • • • • • • • • | T(1,N) |
|--------|--------|--------|-----------------|--------|
| T(2,1) | T(2,2) | T(2,3) | • • • • • • • • | T(2,N) |
| • • • • | • • • • | • • • • |                 | • • • • |
| T(64,1) | T(64,2) | T(64,3) | • • • • • • • • | T(64,N) |
FIG.4(Prior Art)

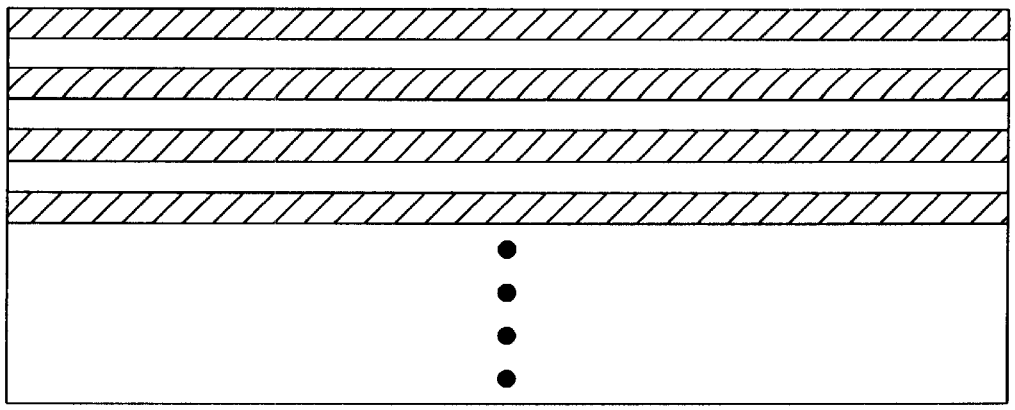
FIG.7
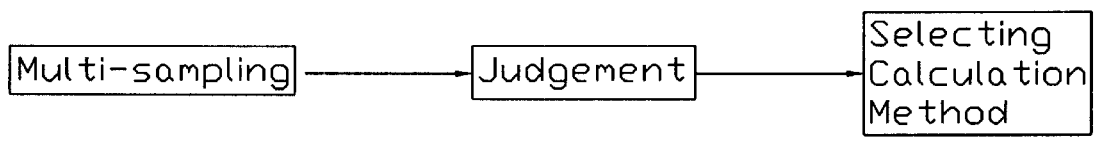
FIG.8
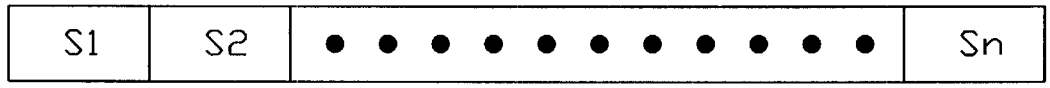
FIG.9A
| S1(1) | S2(1) | • • • • • • • • • • • • | Sn(1) |
|---|---|---|---|
| S1(2) | S2(2) | • • • • • • • • • • • • | Sn(1) |
| •<br>•<br>•<br>• | •<br>•<br>•<br>• | | •<br>•<br>•<br>• |
| S1(64) | S2(64) | • • • • • • • • • • • • | Sn(64) |
FIG.9B

DYNAMIC CALIBRATION METHOD

BACKGROUND OF THE INVENTION

1. Field of the Invention

The present invention relates to a calibration method for color image devices, and in particular to a method of calibrating the color image devices dynamically in order to stabilize the output image.

2. Description of the Prior Art

Many different types of devices exist for sensing color images. These devices can be desktop or hand held scanners, copy machines, facsimile machines, or other similar devices. FIG. 1 shows the interior structure of a transparent scanner 10 in which a light source 20 illuminates image 36 which is reflected by mirror 22 onto transparent lens 24 and then focused onto a photo detector 26. The optical signal received by photo detector 26 is converted into a current signal and output to an analog-to-digital converter (ADC) 28. ADC 28 will then transform the current signal to a digital signal and output the digital signal to an applied specific integrated circuit (ASIC) 30. The data in ADC 30 is stored in memory 32, and also output to host 40 through interface 34. The data from ADC 28 can be handled by firmware, hardware or a host's software.

The main device within the scanner is photo detector 26 shown in FIG. 1. Photo detector 26 is usually a charge coupled device (CCD) with a linear characteristic. In accordance with what is shown in FIG. 2, a photo detector 26 has N sensors, in which each sensor corresponds to a pixel whose width is the degree of optical resolution in units of dots per inch (dpi). Before starting scanning, a scanner will firstly scan a calibration target in order to get a reference of corresponding white or dark for obtaining the reference points conveniently. This procedure is called calibration. FIG. 3 shows a calibration target 60 which is composed of a white calibration area 62 and a dark calibration area 64. Their functions are defined as white reference and dark reference respectively. FIG. 4 shows an output result of the calibration target after being scanned by a photo detector, in which T(1, 1) represents the first pixel scanned by sensor S(1) and T(M, N) represents the Mth pixel scanned by sensor S(N).

An ideal situation would be for all Ts to be identical. Therefore, the conventional method fetches a single point only. However, noise within systems, changeable light source size, dust on the calibration target, attachment of fibers or 20 unknown particles, uneven lighting tube distribution, and system noise enlargement all affect interference during calibration. This causes the calibration result to diverge from the ideal value, and the scanned images to end up with streaking and blocks of not well-distributed phenomena residing on top of them, as shown in FIG. 5. The vertical axis of FIG. 5 is the brightness size, having "LEVEL" as its unit, wherein 0 is the darkest and 255 is the brightest. The horizontal axis represents the position scanned by the sensors. FIG. 5a represents noise interference. FIG. 5b represents lighting not well-distributed. FIG. 5c represents having light gathering phenomena. FIG. 5d represents having dust on top of the calibration target. FIG. 5e represents an ideal situation where brightness versus coordinates is a constant. FIG. 6 is an alternative expression of FIG. 5, wherein its vertical axis is "LEVEL" and its horizontal axis is "COUNT". This expression defines the number of points counted relative to its relative brightness level. It is shown clearly that FIG. 6e is an ideal situation, wherein the figure shown is a delta function.

A well-known prior art solution to the problem of divergence of the calibration result due to interference by dust is taking a simple average of multi-points, or taking an average by skipping adjoining sampling points. As shown in FIG. 7, photo detector 26 reads in the value of oblique-line portions from the calibration target and then takes an average. This method can evade a portion of interference-causing dust, but it is unable to deal with bigger dust or interference caused by different scanners, and also is unable to deal with signals coming from different sources of interference.

SUMMARY OF THE INVENTION

In accordance with the present invention, a method is provided for dynamic calibration that substantially solves all the drawbacks caused by conventional methods by eliminating or substantially reducing the effect caused by interfering factors in order to obtain good output images.

In one embodiment of the present invention, different sampling methods are used by different scanners in order to conform to the different scanners' characteristics. The sampling method can be fixed position multi-sampling, continuous position multi-sampling, discontinuous position multi-sampling, alternatively using fixed position multi-sampling and discontinuous position multi-sampling, or a multi-pixel averaging method. The sampling method is different in accordance with the actual scanner's characteristics.

A further embodiment of the present invention involves analyzing calibration information against different interfering factors. The calibrating information analyzing method can be a direct average method, weighting average method, fixed-range method, or standard deviation range method. The choice of method is decided by the distribution diagram of the multi-sampling.

Furthermore, another embodiment of the present invention uses the calibration method to decide system standards such as the calibration target standard, manufacturing process and environment standard, and a machine's maintenance time.

In accordance with the above embodiments, the present invention provides a dynamic calibration method. This method uses a photo detector to sample the first row of the calibration target and uses the result to obtain a standard deviation $\sigma_r$. A sensor S(N) within the photo detector multi-samples the calibration target and uses the result to obtain a standard deviation $\sigma_s(N)$. Comparing those two standard deviations, if $\sigma_r$ is larger then the direct average of the result of multi-sampling; and if $\sigma_r$ is smaller then examining the distribution diagram of the multi-sampling and selecting a suitable calculating method with respect to different distribution diagrams.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 2 shows a simplified diagram illustrative of a calibration target.

FIG. 3 shows a simplified diagram illustrative of a photo detector.

FIG. 4 shows a simplified diagram illustrative of the scanned calibration target by the photo detector.

FIG. 7 shows the scanned regions of the calibration target in prior art.

FIG. 8 shows a flow chart of the present invention.

FIG. 9a shows a simplified diagram illustrative of a photo detector.

FIG. 9b shows a simplified diagram illustrative of the scanned calibration target by the photo detector.

DESCRIPTION OF THE PREFERRED EMBODIMENT

Figure 1:
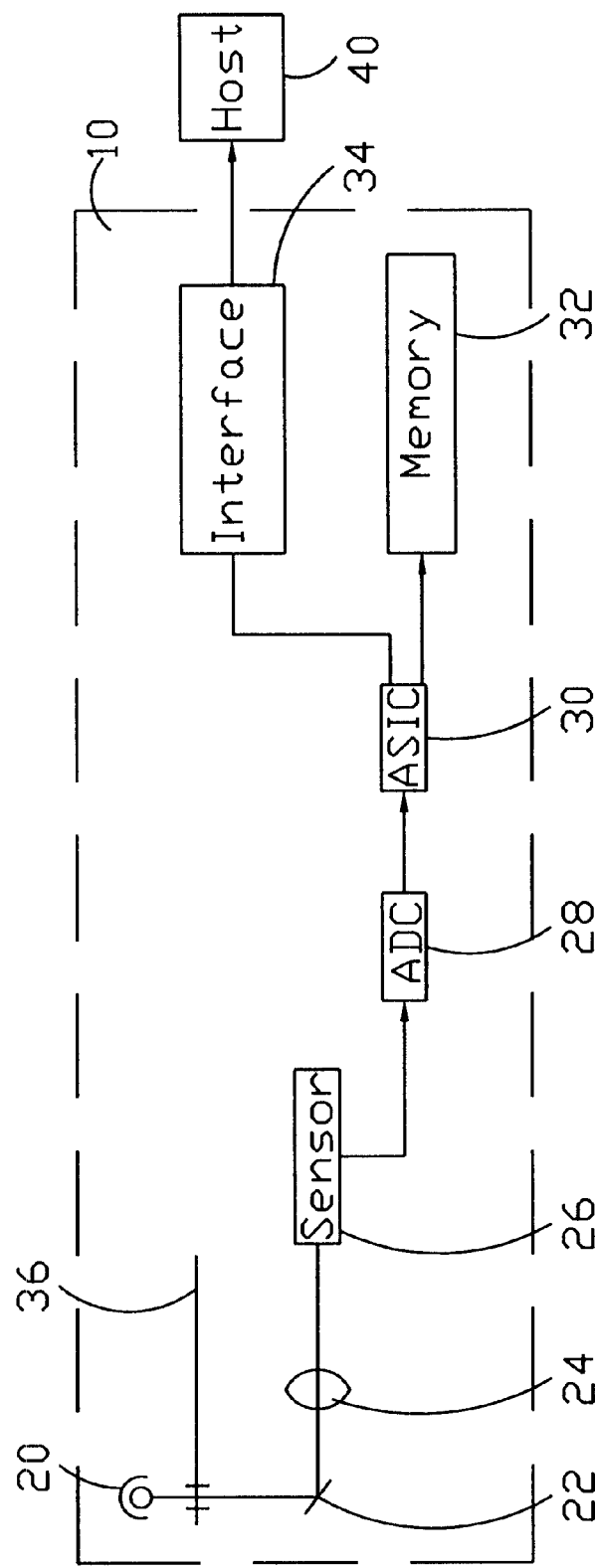
FIG. 1 shows a simplified diagram illustrative of a scanner's interior structure.
Figure 5A:
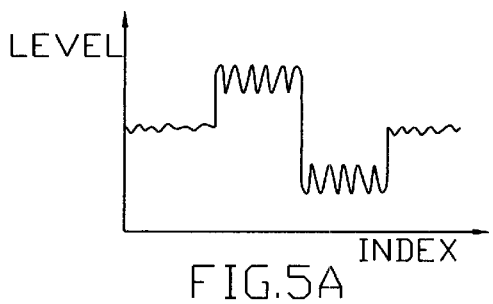
FIGS. 5A–5E show LEVEL versus INDEX diagrams of output result.
Figure 5B:
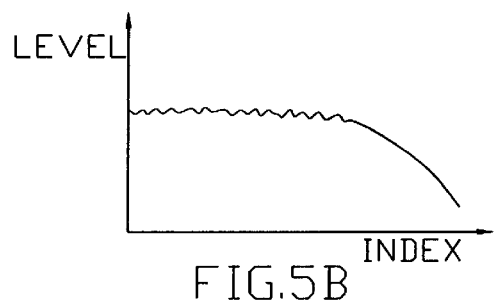
Figure 5C:
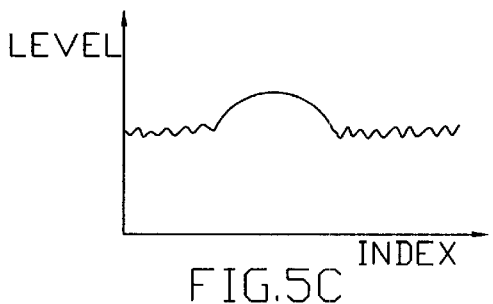
Figure 5D:
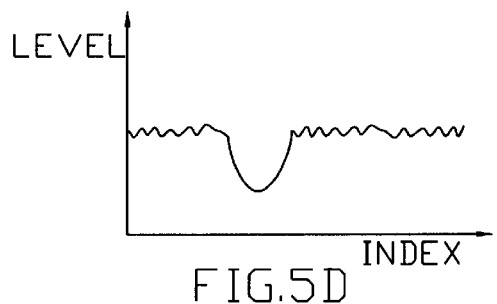
Figure 5E:
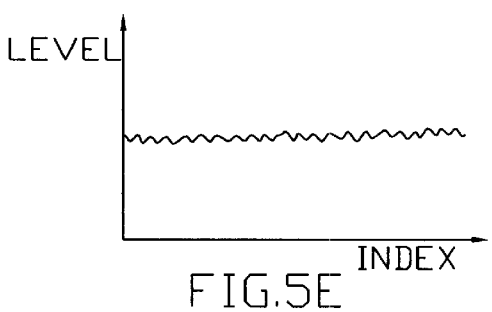
Figure 6A:
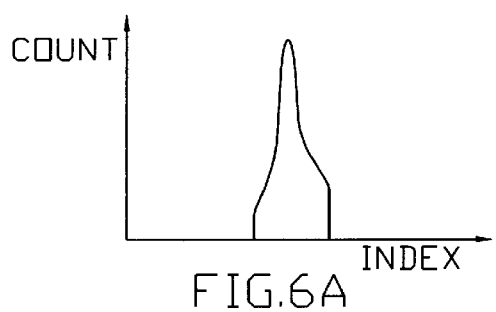
FIGS. 6A–6E show COUNT versus LEVEL diagrams of output result.
Figure 6B:
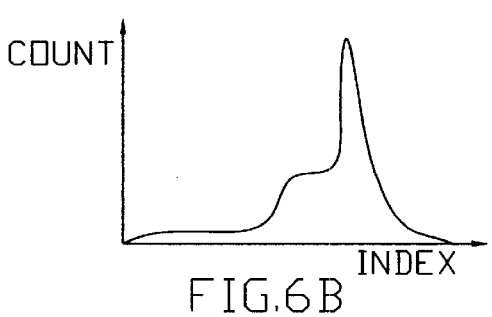
Figure 6C:
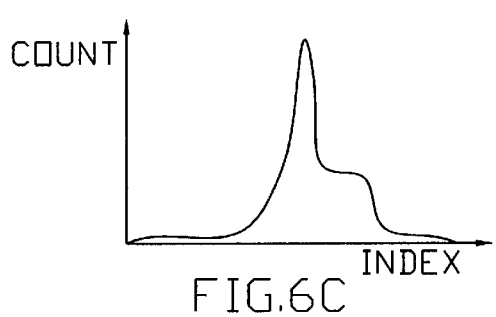
Figure 6D:
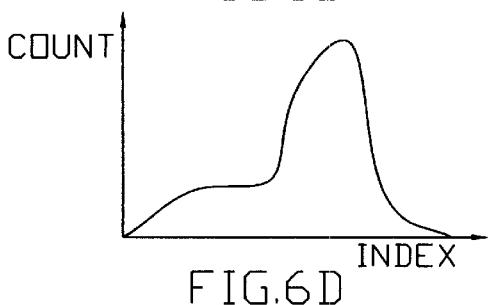
Figure 6E:
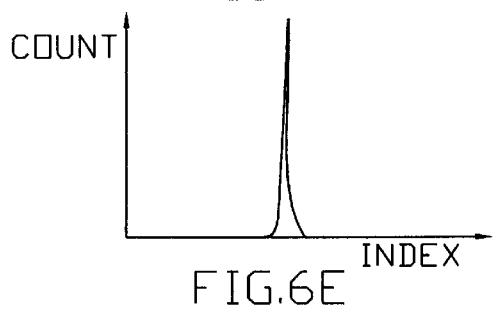

A flow chart showing the preferred method of solving interfering factors according to the present invention is presented in FIG. 8. As shown therein, the photo detector initially multi-samples the calibration target. The sampling result then undergoes a judgement stage in order to select the analysis or calculating method. As shown in FIG. 9a, the photo detector has N sensors, in which the width S corresponds to the degree size of optical resolution. FIG. 9b shows an output result of the calibration target after being scanned by the photo detector, in which $S_N(M)$ represents the Mth pixel scanned by the Nth sensor S. The photo detector samples the first row of the calibration target, where the result can be represented as:

$S=\{S_1(1), S_2(1), S_3(1), \ldots, S_N(1)\}$ and obtains a standard deviation $\sigma_t$ of the result. Basically, the first row of the calibration target is used as a standard and an interference-free output. Therefore, $\sigma_t$ is treated as a standard reference during the calibration procedure. Every sensor can be sampled a plurality of times. Taking N=1 as an example and sampling 64 times, the information can be represented as:

$S_1=\{S_1(1), S_1(2), S_1(3), \ldots, S_1(64)\}$

For those 64 pixels, there are a number of possible multi-sampling methods listed below:

1. Fixed position multi-sampling, that is, a sensor taking 64 samples at the same position can be represented by the following: p1 $S_1=\{S_1(1), S_1(1), S_1(1), \ldots, S_1(1)\}$, or $S_1=\{S_1(2), S_1(2), S_1(2), \ldots, S_1(2)\}$ 2. Continuous position multi-sampling, that is, a sensor taking one sample at every single position can be represented by the following:

$S_1=\{S_1(1), S_1(2), S_1(3), \ldots, S_1(64)\}$

3. Discontinuous position multi-sampling, that is, a sensor taking one sample at every non-adjoining position. The sampling gap is not restricted (examples include: sampling once with one block separation or sampling once with three blocks separation) and can be represented by the following:

$S_1=\{S_1(1), S_1(3), S_1(5), \ldots\}$, or $S_1=\{S_1(2), S_1(4), S_1(6), \ldots\}$, or $S_1=\{S_1(1), S_1(4), S_1(7), \ldots\}$ 4. Using the combination of fixed position multi-sampling and discontinuous position multi-sampling, that is, a sensor taking more than one sample at non-adjoining positions. The sampling gap and sampling times at the same position are not restricted (for example, the sampling gap can be two or three blocks and/or the sampling time can be more than two times), and can be represented by the following:

$S_1=\{S_1(1), S_1(1), S_1(3), S_1(3), S_1(5), S_1(5), \ldots\}$, or $S_1=\{S_1(2), S_1(2), S_1(4), S_1(4), S_1(6), S_1(6), \ldots\}$, or $S_1=\{S_1(1), S_1(1), S_1(4), S_1(4), S_1(7), S_1(7), \ldots\}$ 5. Multi-pixels average method, that is, the sensor continues sampling within adjoining pixels and taking a direct average of the obtained values. Again, the sampling region is not restricted, and can be represented by the following:

$S_1=\{(S_1(1)+S_1(2))/2, (S_1(3)+S1_1(4))/2, \ldots\}$, or $S_1=\{(S_1(1)+S_1(2)+S_1(3)+S_1(4))/4 (S_1(5)+S_1(6)+S_1(7)+S_1(8))/4, \ldots\}$ The above multi-sampling methods are varied in accordance with different scanners or environments. Every scanner must go through certain practical experiments in order to determine which is the most suitable sampling method for each of them. And yet, every scanner only requires one sampling method.

Once multi-sampling is completed, the method of the invention calculates a standard deviation $\sigma_{S1}$ based on the result taken from multi-sampling, and compares the two standard deviations, $\sigma_t$ and $\sigma_{S1}$.

Figure 10:
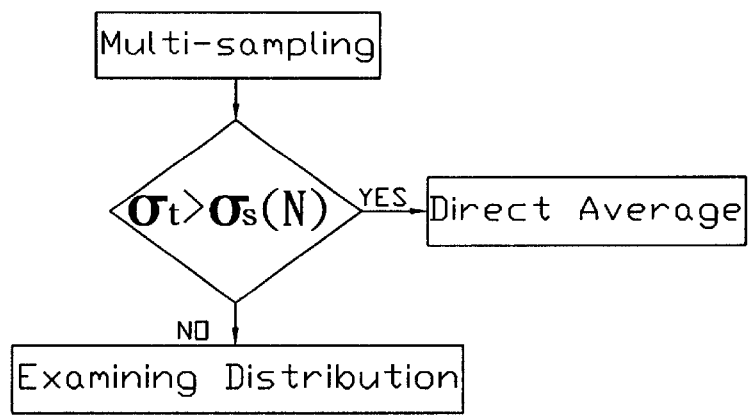
FIG. 10 shows a judgement flow chart of the present invention.

As shown in FIG. 10, if $\sigma_t$ is larger than or equal to $\sigma_{S1}$, which means that the result of continuous sampling is quite good, then the direct average of the result is output. If $\sigma_t$ is smaller than $\sigma_{S1}$, the result of continuous sampling is not good, and the result now needs to examine the distribution diagram of multi-sampling.

Figure 11:
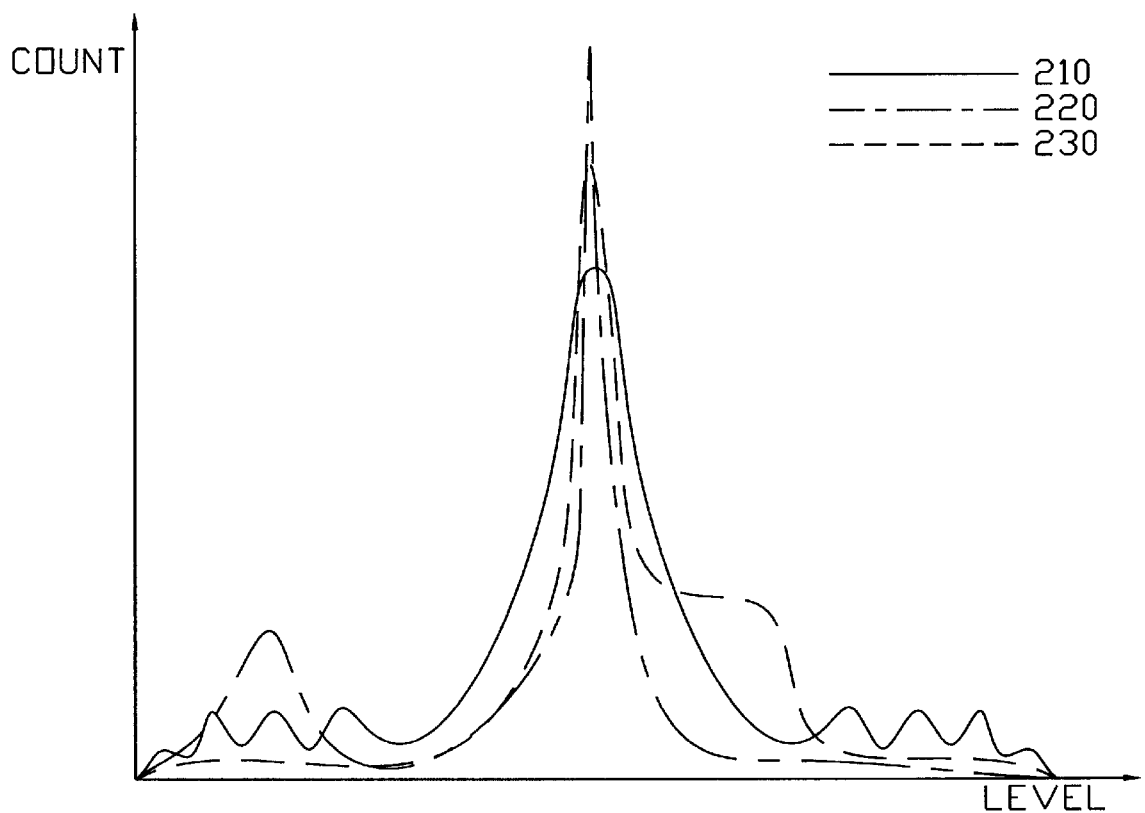
FIG. 11 shows the output result of the photo detector within present embodiments.

The output result of $S_1$ can be expressed by FIG. 11, in which vertical axis represents COUNT and horizontal axis represents brightness (LEVEL). Line 210, line 220, and line 230 represent three possible distributions. Line 210 represents a distribution in which the dominant interference is noise or things like unstable signal; line 220 represents things like water drops with small radius which can gather light and which reside on top of the calibration target; if there is dust on top of the calibration target then light can be blocked, and protrusion would occur on the left hand side of line 220's peak value; line 230 represents dust with larger radius residing on top of the calibration target, thus producing the second peak value further away from the average value. The area under each figure represents the total number sampling points and should be all the same.

Figure 12:
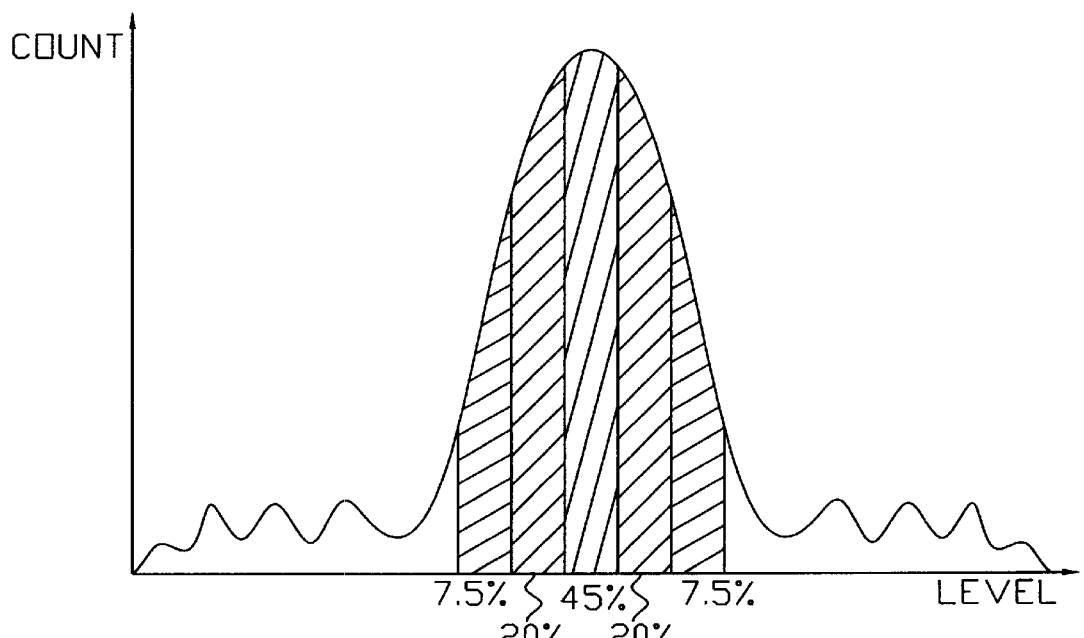
FIG. 12 shows weighting average method within present embodiments.

The step of adopting a weighting average method with respect to line 210 of FIG. 11 is shown in FIG. 12, where the area under line 210 is divided into numbers of sub-regions, different distributive probabilities are used and multiplied by their relative values, and an average is taken. The method of calculation is as follow:

$$45\%*P[S_1(x)]+20\%*P[S_1(x)]+7.5\%*P[S_1(x)],$$

where weight 45% was determined by experiment, and is closely related to the varying characteristic of scanners or environments. $P[S_1(x)]$ is the value of $S_1(x)$ inside the weighted region.

Figure 13:
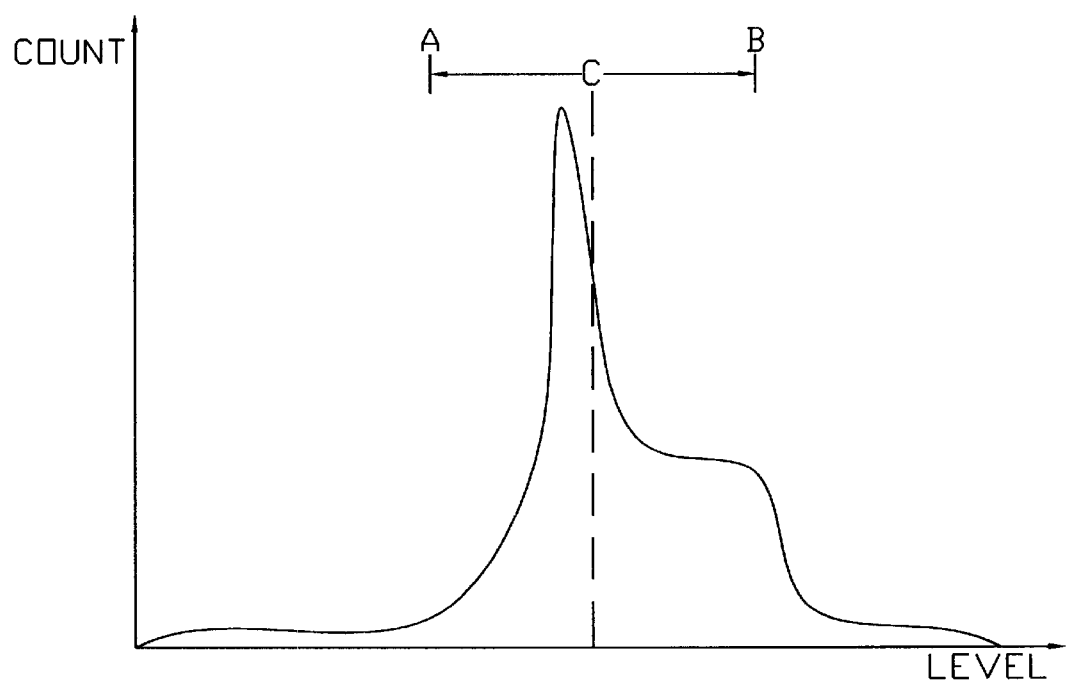
FIG. 13 shows multi-fixed range method within present embodiments.

The step of adopting a fixed range method against line 220 of FIG. 11 is shown in FIG. 13. No matter how large the value of a distributive standard deviation is, a direct average is taken of all values within the range between A and B, where C is the average value. Normally, the values of A and B are decided by the scanner's characteristic, but the range between A and B is fixed in the present embodiment. However, if there is a rise or fall in interference, then the position of the range between A and B can be adjusted.

The step of adopting a standard deviation range method against line 230 of FIG. 11 is used for large radius dust. Due to a long distance between the second and the first peak value, where the source of error is coming from dust with larger radius, these values would not be taken into consideration during the calibration procedure. Therefore, the standard deviation $\sigma_t$ of the first row is sampled and three times the value is used as the selected range.

Within the calibration methods of the present invention, different calibration variables and calculating ways can be used to determine system standards such as a calibration target standard, manufacturing process and environment standard, and the machine maintenance time. There are six calibration variables, as follows:

1. LevelDiff decides an acceptable error, and is used to represent a difference between a calculation result and a desired value, its unit being same as brightness' unit, "LEVEL".
2. Resolution is used to represent the required degree of resolution during calibration in units of dots per inch (dpi).
3. LineCount is used to represent the number of pixels sampled.
4. LevelRange decides an output brightness range, and is used to represent the average of all the points within said brightness range.
5. JumpRatio decides a ratio of discontinuous sampling, and is used to represent the ratio between every pixel and sampling pixel.
6. Yscale decides an optical average, and is used to represent the pixel size for the sensor sampling range.

The six variables above are used to obtain the following:

1. DustCount is the number of sampled points occupied by dust that is the endurable amount of dust residing on top of the calibration target. Once the time usage of a scanner reaches beyond a certain period, and if the amount of dust is over the above value then the scanner needs maintenance.
2. DustSize is the size of dust, that is the endurable size of dust for the scanner within its manufacturing process and environment.
3. CalWidth is the width of the calibration target used to establish the calibration target's standard.

Deriving methods of the established standard are as follows:

DustCount=(LevelDiff*LineCount)/(LevelRange*JumpRation*Yscale),

DustSize=(DustCount*25.4)/Resolution, and

CalWidth=25.4/(Resolution*LineCount*JumpRatio*Yscale), where the unit of length is in millimeters (mm), 1 inch=25.4 mm. According to those three formulas above, Table 1 below can be obtained:

endurable error. That can be achieved by adjusting the selective range and the ratio of discontinuous sampling. When the selective range shrinks, representing an increase in interference extinction, the calibration method is more sensitive to smaller dust. In other words, when the selective range enlarges, the selected points will have bigger errors, and higher vacuum quality is needed for requiring the same endurable error, that is the dust size has to be reduced. Next, looking at the ratio of discontinuous sampling, an increase in ratio means an increase in the number of pixels being skipped by sensors, which shows that the chance of dust being scanned has been reduced and only larger dust will be sensed. When the ratio of discontinuous sampling equals one, representing every pixel being scanned by a sensor, then all the dust size will be read. Accordingly, in order to achieve the required endurable error, dust size needs to be very small.

Although specific embodiments have been illustrated and described, it will be obvious to those skilled in the art that various modifications may be made without departing from what is intended to be limited solely by the appended claims.

What is claimed is:

1. A method of dynamic calibration within color scanners, said color scanners comprising a calibration target which uses as a reference value, a photo detector for detecting light, said method comprising:

sampling the first row of said calibration target by using said photo detector;

generating a standard deviation value of the first row;

multi-sampling against said calibration target within said photo detector;

comparing the standard deviation value of the first row and the standard deviation value of said multi-sampling;

if the standard deviation value of said multi-sampling is smaller than the standard deviation value of the first row, outputting the multi-sampling result by using direct average method without examining the distribution diagram of said multi-sampling;

if the standard deviation value of said multi-sampling is bigger than the standard deviation value of the first row, examining the distribution diagram of said multi-sampling; and making the output brightness (level) at different positions (indices) become approximately a constant by using a corresponding dynamic average method against said distribution diagram of said multi-sampling.

2. The method according to claim 1, wherein said multi-sampling method is accomplished by using identical position multi-sampling.

TABLE 1

| LevelRange | Resolution | LineCount | LevelRange | JumpRatio | Yscale | DustCount | DustSize | CalWidth |
|---|---|---|---|---|---|---|---|---|
| 0.3 | 3000 | 64 | 4 | 4 | 2 | 38.4 | 0.32515 | 4.334933 |
| 0.5 | 3000 | 64 | 4 | 4 | 2 | 64 | 0.541867 | 4.334933 |
| 1 | 3000 | 64 | 4 | 4 | 2 | 128 | 1.083733 | 4.334933 |
| 0.3 | 3000 | 64 | 8 | 4 | 2 | 19.2 | 0.16256 | 4.334933 |
| 0.5 | 3000 | 64 | 8 | 4 | 2 | 32 | 0.270933 | 4.334933 |
| 1 | 3000 | 64 | 8 | 4 | 2 | 64 | 0.541867 | 4.334933 |
| 0.5 | 3000 | 64 | 8 | 1 | 2 | 8 | 0.067733 | 1.083733 |
| 1 | 3000 | 64 | 4 | 1 | 2 | 32 | 0.270933 | 1.083733 |

In accordance with Table 1, one can see that once the dust size is multiplied then the endurable error is also multiplied. It is desirable to obtain the biggest dust size during the manufacturing process and within the same scope of an 3. The method according to claim 1, wherein said multi-sampling method is accomplished by sampling every single position once.

4. The method according to claim 1, wherein said multi-sampling method is accomplished by sampling non-adjoining positions once.

5. The method according to claim 1, wherein said multi-sampling method is accomplished by sampling non-adjoining positions a plurality of times.

6. The method according to claim 1, wherein said multi-sampling method is accomplished by taking a direct average after sampling every position between plural adjoining positions once.

7. The method according to claim 1, wherein within said distribution diagram of multi-sampling, most of the distribution range inside a mean value's standard deviation range presents a natural distribution, and further comprising the step of using a weighting average method to get a desired value.

8. The method according to claim 7, wherein said weighting average method comprises the steps of dividing a region under a distributive relationship into a plurality of sub-regions, and seeking an average by assigning a weight to each sub-region, said weight assigned to each sub-region being determined by a scanner's characteristics.

9. The method according to claim 1, wherein within said distribution diagram of multi-sampling, the distribution range does not present a natural distribution and a portion of said distribution range crosses over a mean value's standard deviation range, and further comprising the step of using a fixed range method to a desired value.

10. The method according to claim 9, wherein said fixed range method comprises the steps of obtaining a fixed range by setting an end point on each side of the mean value, and seeking the average within said fixed range, said fixed range being determined by a scanner's characteristics.

11. The method according to claim 1, wherein within said distribution diagram of multi-sampling, said distribution range does not present a natural distribution and the range between a first peak value and a second peak value is much larger than a standard deviation range, and further comprising the step of using a standard deviation range method to get a desired value.

12. The method according to claim 11, wherein said standard deviation range method comprises the steps of obtaining a range by taking a multiple of a standard deviation on each side of a mean value, and seeking the average within said range, said multiple of said standard deviation being determined by a scanner's characteristics.

13. A method for establishing a calibration standard, said method comprising the steps of:

deciding an acceptable error (LevelDiff) to represent a difference between a calculation result and a desired value;

deciding a number of sampling points (LineCount) to determine a number of points that read on a calibration target;

deciding an output brightness range (LevelRange) to represent an average of all points within said brightness range;

deciding a ratio of discontinuous sampling (JumpRatio) to represent a ratio between every pixel and a sampling pixel;

deciding an optical average (Yscale) to represent a pixel size of a sensor sampling range; and using the following formula to determine the number of sampling points occupied by dust (DustCount):

$$DustCount=(LevelDiff*LineCount)/(LevelRange*JumpRatio*Yscale).$$

14. The method according to claim 13, further comprising the steps of:

deciding a degree of resolution (Resolution) to represent a required degree of resolution during calibration; and using the following formula to determine dust size (DustSize):

$$DustSize=(DustCount*25.4)/Resolution.$$

15. The method according to claim 13, further comprising the following formula to determine the width a calibration target (CalWidth):

$$CalWidth=25.4/(Resolution*LineCount*JumpRatio*Yscale).$$

* * * * *